(12) United States Patent
Haar et al.

(10) Patent No.: US 8,409,868 B2
(45) Date of Patent: Apr. 2, 2013

(54) TEST ELEMENT FOR DETERMINING A BODY FLUID AND MEASUREMENT METHOD

(75) Inventors: Hans-Peter Haar, Wiesloch (DE); Carina Horn, Biblis (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/224,751

(22) Filed: Sep. 2, 2011

(65) Prior Publication Data

US 2012/0045843 A1 Feb. 23, 2012

Related U.S. Application Data

(63) Continuation of application No. PCT/EP2010/001752, filed on Mar. 19, 2010.

(30) Foreign Application Priority Data

Mar. 20, 2009 (EP) .................................... 09004009

(51) Int. Cl.
*G01N 21/77* (2006.01)
*G01N 33/48* (2006.01)
*G01N 33/66* (2006.01)

(52) U.S. Cl. ............ 436/169; 436/63; 436/95; 436/164; 435/14; 435/287.1; 435/287.7; 422/400; 422/420; 422/82.05; 422/68.1

(58) Field of Classification Search .................... 436/63, 436/95, 164, 165, 169, 170, 172; 435/14, 435/287.1, 287.7, 287.8, 288.7; 422/400, 422/420, 421, 422, 423, 68.1, 82.05, 82.08, 422/82.09, 82.12

See application file for complete search history.

(56) References Cited

U.S. PATENT DOCUMENTS

| 5,972,715 | A | * | 10/1999 | Celentano et al. ............ 436/164 |
| 6,055,060 | A | | 4/2000 | Bolduan et al. |
| 6,880,968 | B1 | * | 4/2005 | Haar .............................. 374/131 |
| 8,105,841 | B2 | * | 1/2012 | Blais et al. ..................... 436/147 |
| 2004/0136871 | A1 | | 7/2004 | Pachl et al. |
| 2005/0123441 | A1 | * | 6/2005 | Unkrig et al. ................... 422/56 |
| 2008/0014655 | A1 | | 1/2008 | Horn |

FOREIGN PATENT DOCUMENTS

| DE | 10 2004 051 830 A1 | 4/2006 |
| EP | 0 819 943 A2 | 1/1998 |
| EP | 1 411 346 A2 | 4/2004 |

OTHER PUBLICATIONS

International Preliminary Report on Patentability, International Application No. PCT/EP2010/001752, 14 pages, Oct. 19, 2011.
Roger J. McNichols et al., "Optical Glucose Sensing in Biological Fluids: An Overview", Journal of Biomedical Optics, Jan. 2000, 6 pages, vol. 5 No. 1.

* cited by examiner

*Primary Examiner* — Maureen Wallenhorst
(74) *Attorney, Agent, or Firm* — Krieg DeVault LLP (57) ABSTRACT

A test element for determining a body fluid is provided. The test element, in particular for determining the blood glucose level, includes a detection region which is charged with a reagent sensitive to the body fluid. A function element is arranged in or adjacent to the detection region for detecting at least one status parameter for the detection region, such that the functional element can be evaluated by means of a status measurement. A method for measuring the test element is also disclosed.

18 Claims, 8 Drawing Sheets

Fig. 9b

TEST ELEMENT FOR DETERMINING A BODY FLUID AND MEASUREMENT METHOD

CROSS-REFERENCE TO RELATED APPLICATIONS

This application is a continuation of International Application No. PCT/EP2010/001752 filed Mar. 19, 2010, which claims priority to EP Application No. 09004009.8 filed Mar. 20, 2009. Each of the referenced applications is incorporated herein by reference in its entirety.

FIELD OF THE INVENTION

The invention relates to a test element for determining a body fluid, in particular for determining blood sugar, and a measurement method of such a test element.

BACKGROUND

Such test elements are used in order to determine body fluids, in particular for detection of a body fluid as such or of a component contained by it. For example, the determining of the body fluid takes place in connection with such a test element with an optical evaluation. Various optical measurement parameters can be evaluated here, for example the light emission in the form of a fluorescence or a phosphorescence or the light absorption. The optical measurement methods have proved to be expedient for some test elements in the form of test strips, in particular in connection with the examination of small blood volumes. They can also be used advantageously in ergonomically configured test strips.

For detection of the body fluid or of a component contained by it, the test elements regularly have a so-called detection zone, in which usually a chemical detection reaction of the body fluid or of one of its components takes place with a reaction system present in the reaction zone of the test element, so that one or more reaction products can be subsequently detected by measurement technology, in particular with the aid of an optical measurement.

In order to draw the correct conclusion with regard to the determining of the body fluid by means of the evaluation of the test element, quality and accuracy of the measurement process are of particular importance. Thus, the use of particular test elements is permitted only in temperature ranges which are specified for this, because an appropriate determining of the body fluid is only guaranteed with sufficient certainty in these temperature ranges. In a determining of blood sugar, for example the hematocrit value and therefore its influence on the measurement is temperature-dependent. In connection with test elements for determining blood sugar, therefore measurements and corrections derived herefrom in the evaluation of the measurement were proposed on the basis of the electrochemistry or the amperometry by means of the impedance method.

The document EP 1 411 346 A2 describes a method for the detection of an underdosing of an analytical test element and a system and a test element which are suitable for detecting an underdosing.

The document DE 10 2004 051 830 A1 describes a system for a luminescence detection of an analyte in a fluid sample (e.g. blood).

In the document EP 0 819 943 A2 an analysis system is described for the evaluation of analytical test elements.

SUMMARY

There is provided an improved test element for determining a body fluid and an improved measurement method of the test element, by which the accuracy of the determining of the body fluid is optimized. Additional effort in the evaluation of the test element is to be minimized as much as possible or even avoided here.

According to one aspect, there is provided a test element for determining a body fluid, in particular for determining blood sugar, with a detection zone which is charged with a reagent sensitive to the body fluid, wherein in the detection zone and/or adjacent thereto a function element is arranged which is able to be evaluated for registering at least one status parameter for the detection zone by means of a status measurement.

According to another aspect, a measurement method of a test element configured for a determining of a body fluid, in particular of a test element configured for determining blood sugar, in which one or more status parameters are registered for a detection zone which is charged with a reagent sensitive to the body fluid, by measurement signals for one or more function elements arranged in the detection zone and/or adjacent thereto being measured by means of a status measurement.

The test element and method create the possibility of directly obtaining status information for the detection zone of the test element in an efficient manner experimentally. The status information can then be evaluated in various ways. For example, a decision can be made by means of the status information as to whether or not a test element on the basis of its characteristics in the detection zone is still at all suitable for a determining of the body fluid. If deviations from a status defined as a normal or minimum measurement are ascertained, the test element can be rejected. However, a consideration of the status information can also be provided in the actual determining of the body fluid, for example in the form of a correction of registered measurement signals. In this way, for example, different reaction courses can be considered for the detection reaction. The status measurement used for registering the at least one status parameter for the detection zone, by which the function element is able to be evaluated, can take place in connection with the determining of the body fluid itself, for example for the purpose of the mentioned measurement correction. However, a separate use of the status measurement can also be provided, for example for checking the quality of a test element before the determining of the body fluid.

The function element may be a substance, a compound or a substance mixture. The function element can be arranged on the test element exclusively in the detection zone, exclusively adjacent thereto or both in the detection zone and also adjacent thereto.

The most varied of measurement methods known as such are available for the status measurement, which can be called upon according to the configuration of the function element contained by the test element.

In one embodiment, it may be provided that the function element is an inert function element as regards reaction chemistry with respect to a detection reaction on determining the body fluid. In this embodiment, the function element is not altered chemically itself through the detection reaction on determining of the body fluid. Alternatively, or in addition to this, provision can be made that the function element also for its part is configured not influencing the reaction chemistry of the detection reaction.

In another embodiment, it is provided that the function element is a function element which is sensitive to a reaction parameter of the detection reaction on determining the body fluid. A reaction parameter of the detection reaction, which can be checked by means of an experimental evaluation of the function element is, for example, the temperature before, during or after the detection reaction in the detection zone. If for example a light-emitting function element is used as function element, its light emission behaviour can be evaluated during the detection reaction as indicator for the temperature in the detection zone. For example, the chronological course of the fading of a fluorescence or of a phosphorescence after a previous stimulation can be evaluated as temperature indicator. So-called europium complexes such as europium chelates are to be mentioned by way of example as usable function elements in this context. In such europium complexes, the fluorescence fading behaviour depends on the temperature (cf. for example Katagiri et al., J. Alloys and Comp., 408-412, 809-812 (2006); Wolfbeis et al., Anal. Chem., 78, 5094-5101 (2006); Khalil et al., Sens. Act. B. Chemical, 96, 304-314 (2003); Wolfbeis et al., Analyst, 132, 507-511 (2007)). Provision can be made in this connection to embed the europium complexes into a polymer matrix, for example a polyvinyl methyl ketone matrix. In this way, polymer globules are able to be produced, which on production of the test element can be introduced into the detection zone and/or adjacent thereto. Depending on the function element which is used, one or more reaction parameters can thus be evaluated for the detection reaction on determining the body fluid experimentally by means of a measurement in a direct manner.

In another embodiment it is envisaged that the function element is a function element which is sensitive to a test element parameter. In this embodiment, the test element is configured alternatively or in addition to other configurations with the aid of the function element, such that parameters of the test element can be registered by means of the status measurement for the function element. Here, for example, the functional integrity of the test element is able to be checked. For example, the layer thickness of one or more layers can be evaluated with the aid of the function element, incorporated into the layers, by means of the status measurement. Thus, in an embodiment, the function element can be a light-emitting element. Within the framework of the status measurement, by means of the intensity of the measured light emission the thickness of a layer can be deduced, in which the function element is situated on the test element. Also, provision can be made that within the framework of the status measurement a measured light intensity is compared with comparative values, which were registered for the test element at an earlier time, for example immediately after production. In this way, it is able to be ascertained whether in the layer in which the function element is situated a change has taken place, influencing the layer thickness, which can make the test element, for example, unusable. If a change is ascertained, which still leaves the test element in a usable state, the layer thickness information can be used for the correction of measurement results which are registered within the framework of the determining of the body fluid.

Another embodiment makes provision that the function element is a function element which is able to be evaluated for registering the at least one status parameter for the detection zone by means of an optical status measurement. In this way, the status measurement is able to be evaluated with the aid of a measurement technology, namely an optical measurement which is already available in evaluation equipment for such test elements, for example for the detection of a colour change on determining the body fluid. The function element can be configured to emit light in the form of a fluorescence or a phosphorescence. Also provision may be made to register the optical measurement signals, which are registered within the framework of the optical status measurement, in a time-resolved, spectrally resolved and/or intensity-dependent manner. The optical status measurement can be adapted depending on the function element which is used and the status information able to be evaluated herewith.

In another embodiment, it may be provided that the function element is a function element able to be evaluated for registering the at least one status parameter for the detection zone by means of a time-resolved optical status measurement. A further development can make provision that the function element is a function element able to be evaluated for registering the at least one status parameter for the detection zone by means of an intensity-dependent optical status measurement. The time-resolved optical status measurement and the intensity-dependent optical status measurement can be combined, if required, with a spectral resolution, in which the registered optical measurement signals are evaluated in a wavelength-dependent manner.

Another feature makes provision that the function element is at least partly mixed with the reagent. With the aid of the mixing of function element and reagent, the function element is at least partly embedded into the reagent, which further assists a direct registering of status parameters for the detection zone.

In another embodiment, it is envisaged that in the detection zone or adjacent thereto, the function element is arranged in several zones which are separated from each other spatially. In this way, it is made possible to register status parameters for different spatial zones in the detection zone or adjacent thereto. In this connection, for the measurement technology used for the evaluation of the function element, provision may be made to use one or more detectors, in order to examine experimentally the several zones which are separated from each spatially. In the case of an optical status measurement, several optical sensors may be provided, for example in the form of sensor diodes.

One embodiment makes provision that in the detection zone or adjacent thereto a further function element is arranged, able to be evaluated for registering a further status parameter for the detection zone by means of a further status measurement. The use of different function elements can contribute to registering different status parameters for the detection zone. Alternatively or in addition, however, provision may also be made that with the aid of different function elements identical status parameters are registered for the detection zone, so that this status information is obtained in various ways and therefore with a higher reliability. The further function element may, if required, be formed in accordance with the various previously described configuration possibilities for the function element. In the case of an optical status measurement and of suitable function elements for this, provision may be made for example that the different function elements emit light of various colours, so that this can be registered and evaluated separately in a simple manner with the aid of a wavelength filtering.

Another embodiment provides for multi-layer structure, formed at least in the detection zone. In the multi-layer structure, the function element can be arranged in one or ii several layers. Also, provision may be made in an embodiment that different function elements are embedded into one or into several layers. In this way, the test element is able to be configured according to the task, in order to register status information for the detection zone.

Additional embodiments of the method for measurement of a test element, configured for determining a body fluid, are explained in further detail below.

In one embodiment, provision can be made that as status parameter a reaction parameter is registered for a detection reaction on determining the body fluid in the detection zone. For example, with the aid of an optical status measurement for a test element which is able to be evaluated in this manner, the temperature for the detection reaction can be registered directly in the detection zone.

One development can make provision that as status parameter a test element parameter is registered for the test element. Test element parameters which can be registered in this manner are, for example, the thickness of layers of the test element, the mechanical integrity of zones of the test element or else layer thickness variations. Provision can be made to evaluate in various ways a measurement signal which is registered for a function element, in order to register different status parameters. In the case of an optical status measurement, in which optical measurement signals are registered for function elements arranged in the test element, the optical signal, for example in the form of a fluorescence- or phosphorescence signal, can be registered in a time-resolved and intensity-dependent manner, in order to thus for example obtain information concerning the temperature in the detection zone on the one hand, and the layer thickness on the test element on the other hand.

Another development makes provision that the measurement signals are compared with comparative signals. As comparative signals, for example, measurement values are available which were registered for the test element at an earlier time and/or under other environmental conditions. For example, for the test element, when it is a dry chemical test element, a measurement can take place in the dry initial state, for example immediately after production. These measurement signals can then be compared with currently registered measurement signals, if a sample of the body fluid which is to be determined is placed onto the test element, or if this is intended. In connection with reaction parameters for the detection reaction, the measurement signals can be compared with predetermined values, which must be fulfilled in order to ensure the correct determining of the body fluid. If a reaction parameter lies outside the predetermined values, for example in the form of a temperature which is too high or too low, this can be reacted to in the evaluation equipment for the test element, for example by means of a cooling or a heating for the test element. Thus, for typical test elements, for example ranges of application of between approximately 15° C. and approximately 35° C. are predetermined. By means of the techniques which are proposed here, test elements are created which are configured for a field of application in the range of between approximately 5° C. and 50° C.

In connection with test element parameters, in the case of a deviation of comparative values, for example owing to a batch fluctuation, a different course of the detection reaction can be expected, which can then be taken into consideration in the evaluation of the determining of the body fluid.

In one embodiment, provision can be made that as reaction to the registering of the one or of the several status parameters for the detection zone, reaction parameters influencing the detection reaction on determining the body fluid are altered. The registering of the one or of the several status parameters can take place before the determining of the body fluid, in order to then set corresponding parameters for the detection reaction in the evaluation equipment for the test element. However, a registering of the status parameters during the detection reaction can also be provided additionally or alternatively thereto.

Another embodiment makes provision that the status measurement is carried out as an optical measurement, in which optical measurement signals are measured. The optical measurement is usually carried out by excitation light of a particular colour or of a mixed colour being irradiated onto the detection zone of the test element, whereby the one or the several function elements are stimulated and emit light themselves, for example in the form of fluorescence or phosphorescence. The emitted light can then be registered with the aid of one or several detectors in a spectrally resolved, time-resolved and/or intensity-dependent manner, in order to obtain different status- or measurement information. A light emission can, however, also be stimulated by the detection zone being acted upon with an electric current. A chemoluminescence can also be evaluated for obtaining status information.

BRIEF DESCRIPTION OF THE DRAWINGS

The invention is explained in detail in the following by means of embodiments illustrated in the figures.

DETAILED DESCRIPTION

Figure 1:
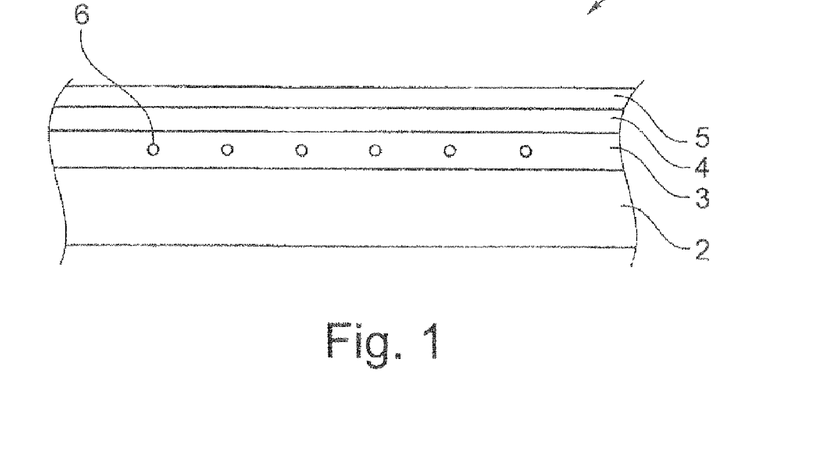
FIG. 1 is a diagrammatic illustration of a multi-layer structure of a test element for determining a body fluid.

FIG. 1 shows a diagrammatic illustration of a multi-layer structure of a test element 1, which is configured for a determining of a body fluid, in particular determining blood sugar. On a light-permeable carrier substrate 2, which in an embodiment is formed from a carrier film of polycarbonate with a thickness of approximately 30 µm to approximately 150 µm, there is situated an active layer 3, which in turn contains the reaction chemistry for the determining of the body fluid, for example a reagent in the form of an enzymatic system. The active layer 3 is formed for example with a thickness of approximately 10 µm. In the active layer 3, the detection reaction takes place, for example in the form of a colour reaction, which is then able to be evaluated by means of an optical measurement in an evaluation apparatus arranged for the test element. Various reaction systems are known for the determining of a body fluid as such and with regard to its ability to be evaluated, which preferably takes place optically, for which reason this is not entered into in further detail.

Above the active layer 3, a further layer 4 is formed which in an embodiment contains pigments, for example in the form of $TiO_2$ or $ZrO_2$. The further layer 4 may have, for example, a thickness of approximately 10 µm. With a possible configuration of the test element 1 for a blood determination, the further layer 4 serves for the separation of the erythrocytes. In the optical evaluation of the test element, the incorporated pigment reflects irradiated measurement light in a diffuse manner. Finally, above the further layer 4, a net layer 5 is produced, which serves for the spreading of the blood.

Figure 9A:
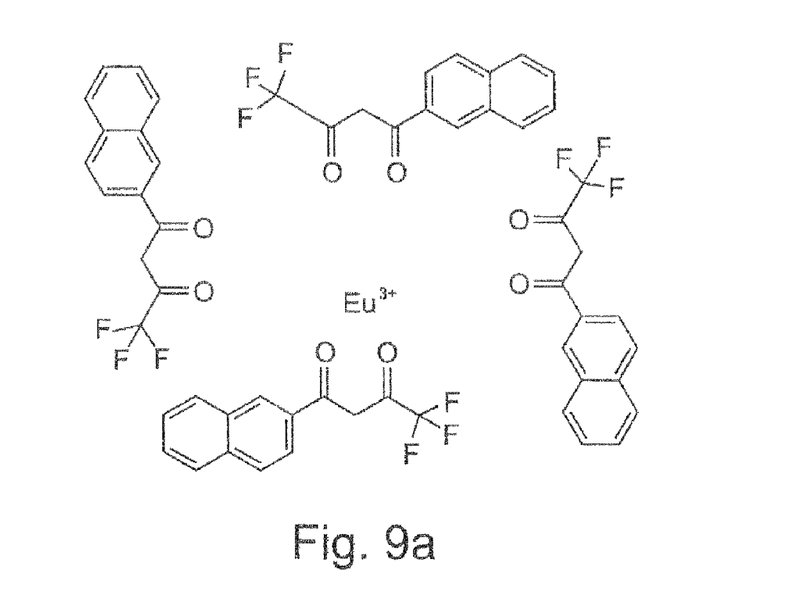
FIGS. 9a, 9b are structural formulae of further europium complexes which are able to be used as functional element.
Figure 9B:
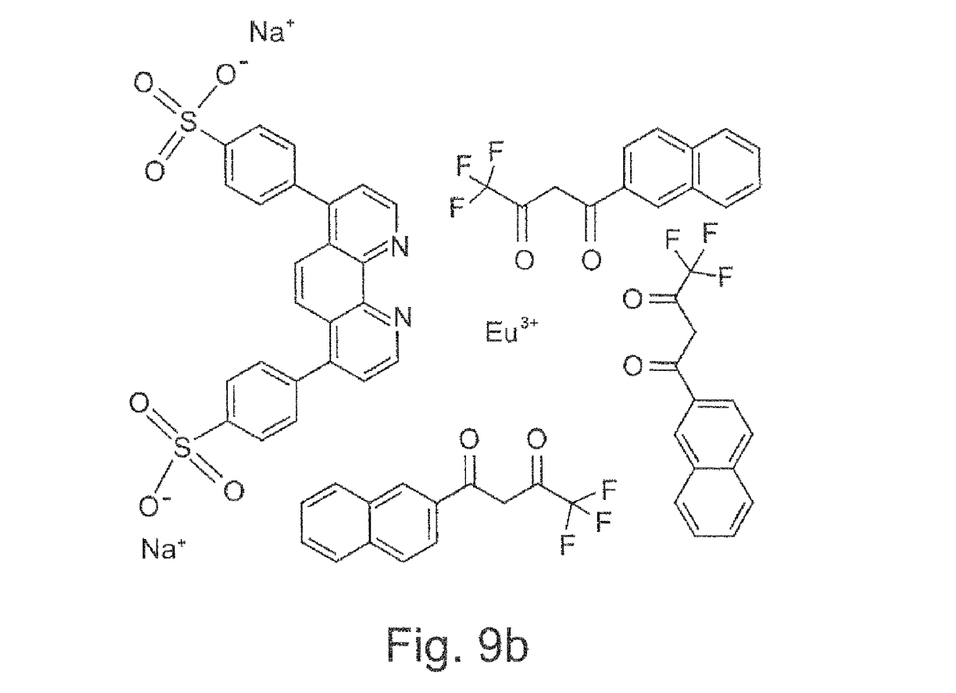

Function elements 6 are incorporated into the active layer 3, these being, in a possible embodiment, globules of a polymer, into which europium complexes are embedded. Two embodiments for such europium complexes are shown in FIGS. 9a and 9b. The europium complexes serve as function elements which on optical stimulation emit light which can be registered by one or several optical sensors.

Figure 2:
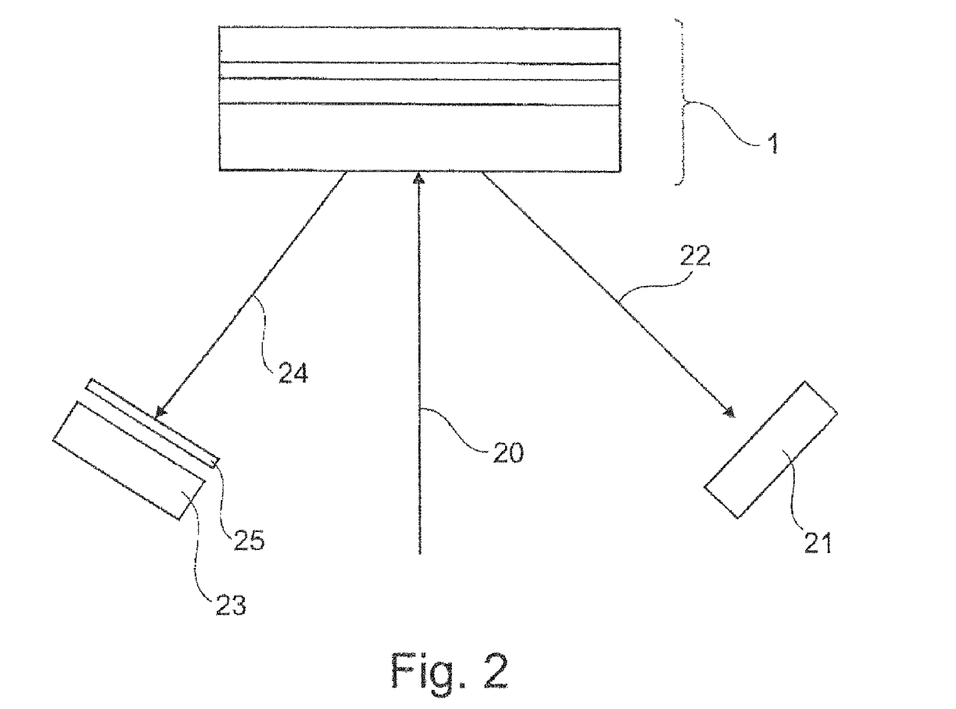
FIG. 2 is a diagrammatic illustration of a measurement arrangement for the optical measuring of a test element for determining a body fluid.

FIG. 2 shows a diagrammatic illustration of a measurement arrangement for the optical measuring of a test element for determining a body fluid. Measurement light 20, which has a wavelength of 365 nm, is irradiated onto a test element 1, which in the illustrated embodiment is constructed in accordance with the description in connection with FIG. 1. Light 22, reflected in a diffuse manner on the test element 1, is detected via a measurement channel 21, The signal registering takes place in a time-resolved trimmer. The chronological intensity course of the light 22, reflected in a diffuse manner, is detected for various glucose concentrations on the test element 1.

Via a further reception channel 23, fluorescent light 24 of the europium complexes is detected in a time-resolved and intensity-dependent manner. The measurement light 20 is masked out in a wavelength-selective manner with the aid of an edge filter 25. For example, an edge filter can be used, which is permeable for wavelengths >450 nm The fluorescence signals which are measured with the aid of the further reception channel 23 are then evaluated with the aid of an electronic evaluation device (not illustrated). For example, the fluorescence fading behaviour can be evaluated. Here, one or more fading times are determined for the fluorescence of the europium complexes, stimulated with the aid of the measurement light 1, in the test element 1. Alternatively or additionally, the phase shift between the measurement light 20 and the fluorescence light 24 can be determined by means of the use of the lock-in technique. Then, with the aid of conventional techniques, information concerning the fluorescence fading behaviour can be deduced from the phase shift.

Figure 3:
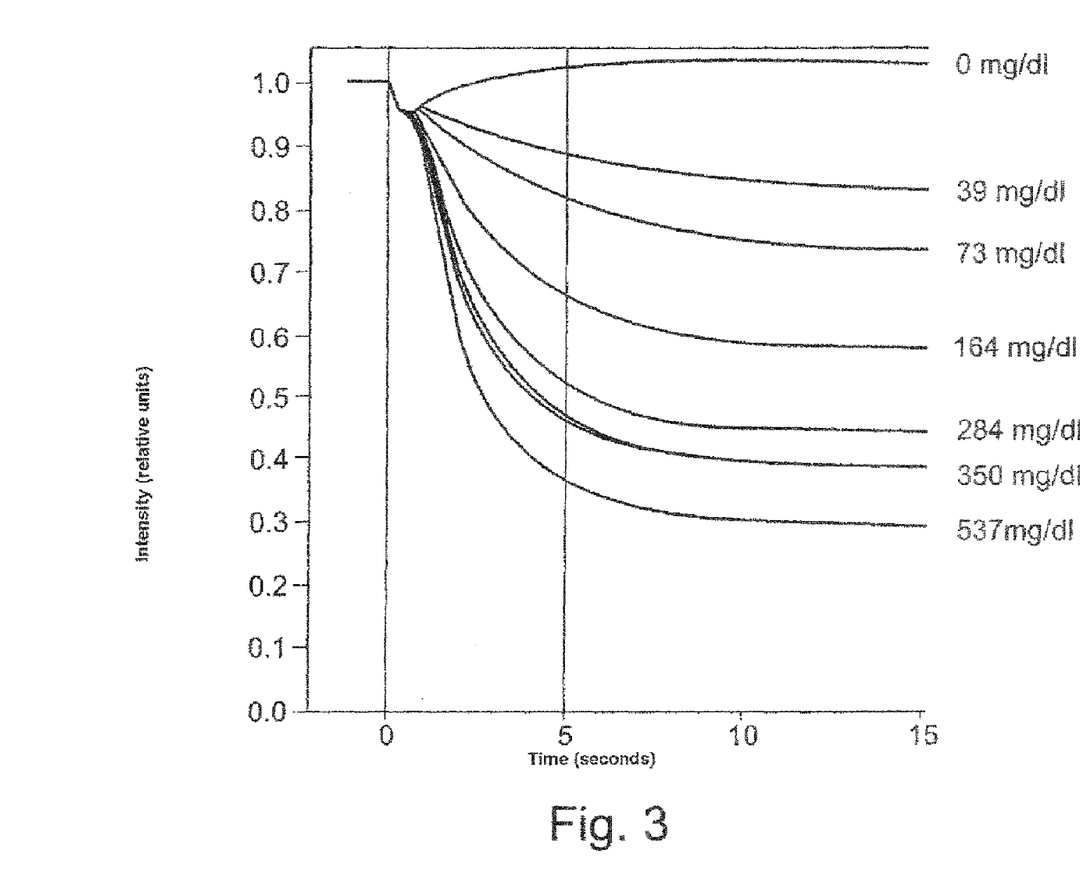
FIG. 3 is a graphic representation of a fluorescence course as a function of time for various glucose concentrations.

FIG. 3 shows a graphic representation of an intensity course as a function of time for various glucose concentrations. The intensity course is represented for the diffuse reflection on optical examination of a test element charged with a blood sample using the measurement arrangement in FIG. 2. Here, the test element was charged with a blood sample at the instant zero, so that the initially dry test element becomes wet. After this, the reaction of the formation of a species begins, for which then the optical examination is carried out, for example by means of registering the diffuse reflection, which is also designated as remission. Several intensity courses are illustrated for different glucose concentrations.

Figure 4:
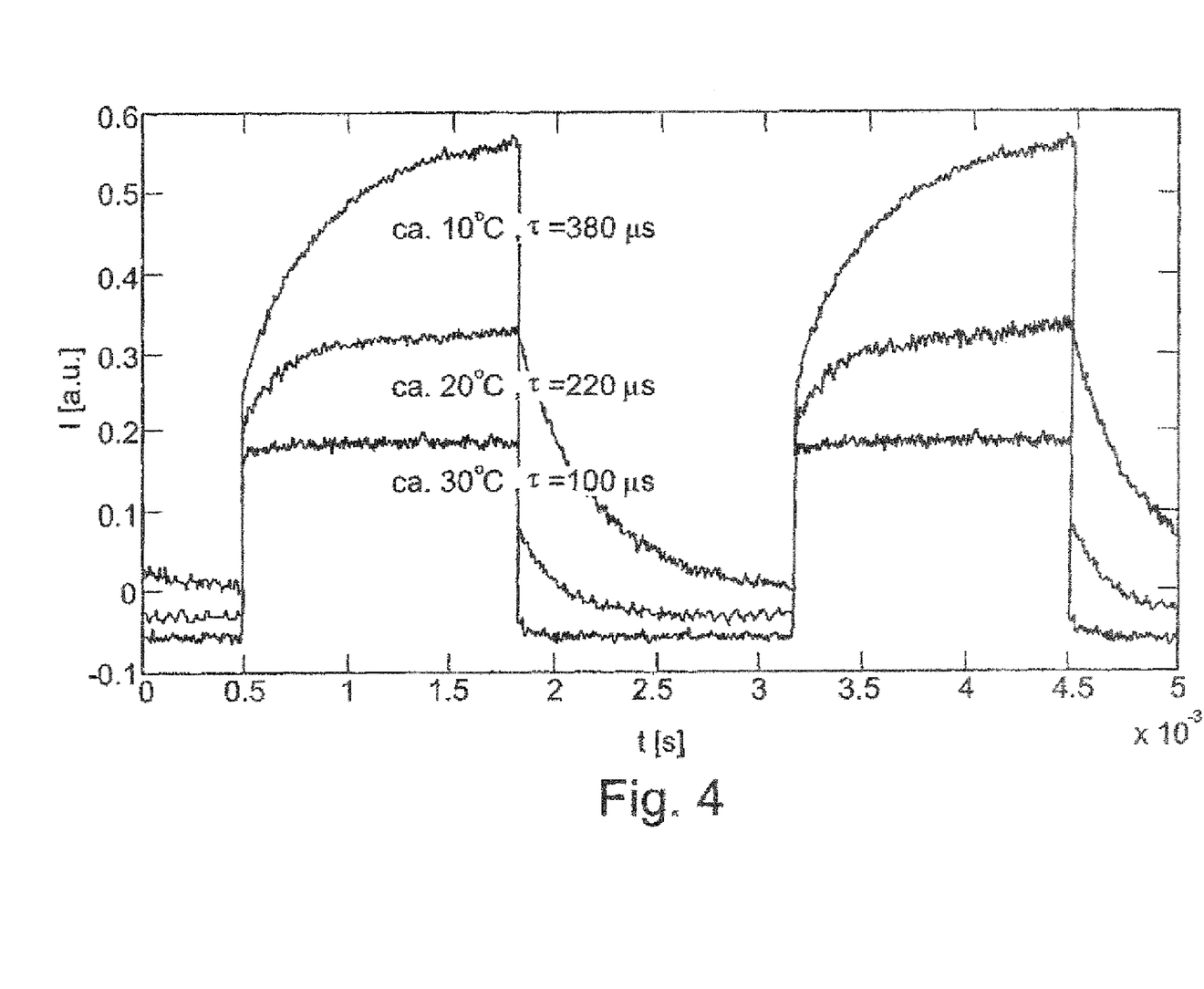
FIG. 4 is a graphic representation of fluorescence curves as a function of time for different temperatures.

FIG. 4 shows a graphic representation of fluorescence curves as a function of time for different temperatures. It can be seen that at different temperatures, namely approximately 10° C., approximately 20° C. and approximately 30° C., the fluorescence behaviour is different in its chronological course. The measurement signals were registered after an optical excitation with excitation light of approximately 360 nm. The detector was situated perpendicularly above the sample at a distance of approximately 3 mm. The different fluorescence behaviour therefore enables a conclusion to be drawn concerning the temperature in the environment of the light-emitting elements. For the test element 1 illustrated in FIG. 1, this means that with the aid of the function elements 6 of the active layer 3 comprised by the detection zone, the temperature can be determined directly, which is present in this zone for the detection reaction on determining of the body fluid. As a function of the evaluation of the time behaviour of the fluorescence and of the temperature conditions concluded herefrom, the conditions for the determining of the body fluid can then be set or altered as required in the evaluation equipment.

Figure 5:
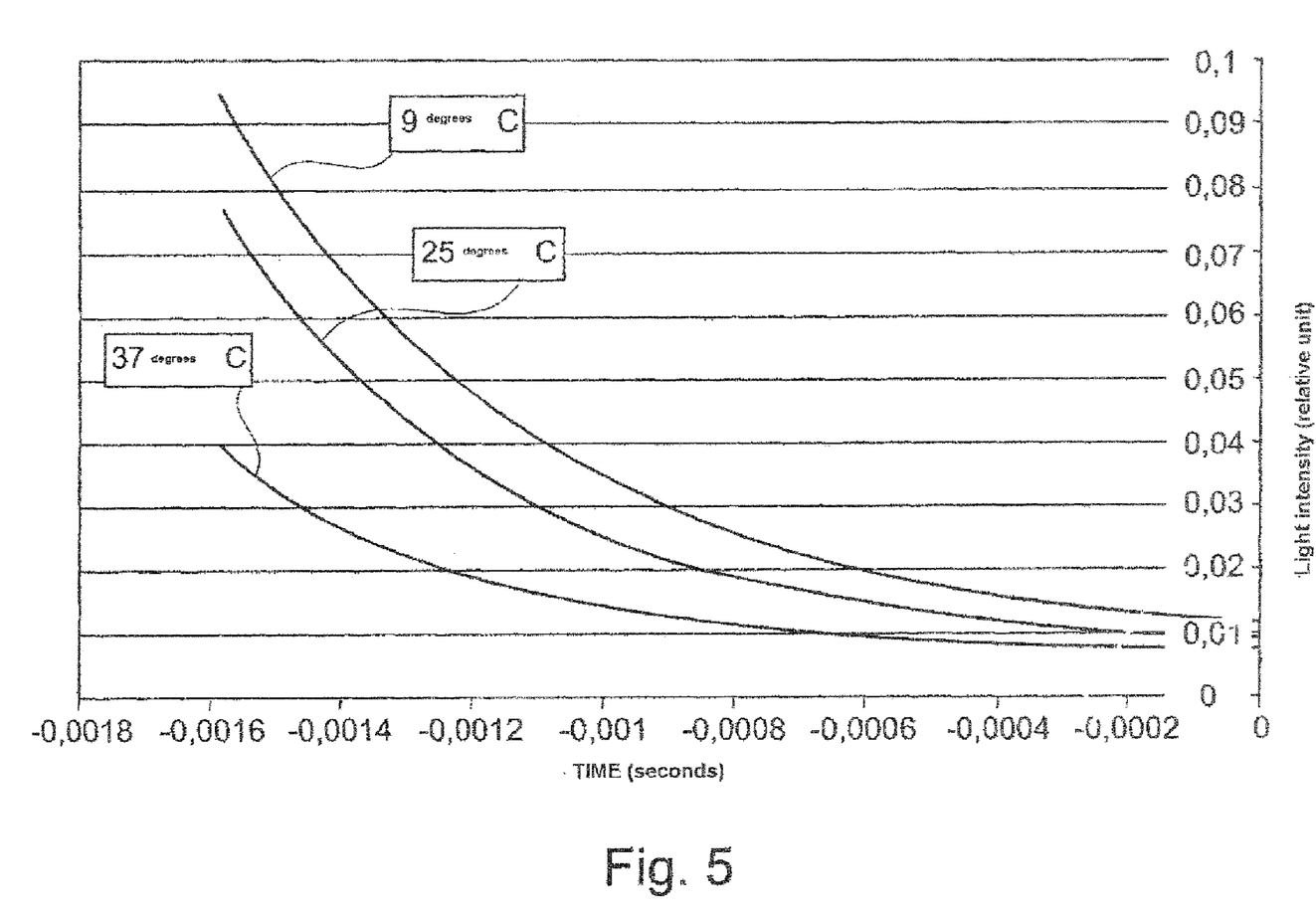
FIG. 5 is a graphic representation of the measured fluorescence fading behaviour as a function of time at various temperatures for the europium complex in FIG. 7.
Figure 7:
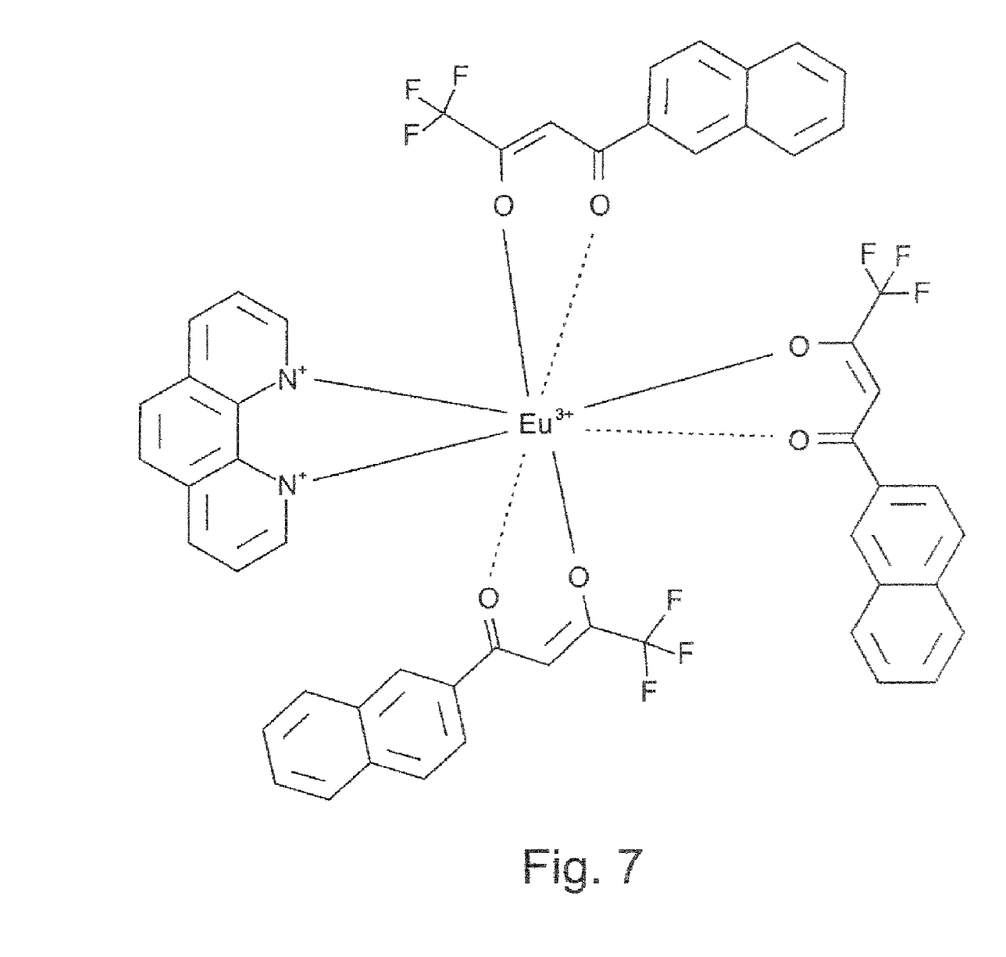
FIG. 7 is the structural formula of a europium complex.

FIG. 5 shows a graphic representation of the measured fluorescence fading behaviour as a function of time at various measurement temperatures for the europium complex able to be used as function element in FIG. 7. The intensity of the fluorescent light of the europium complex was measured at 9° C. (upper curve), 25° C. (central curve) and 37° C. (lower curve).

Figure 6:
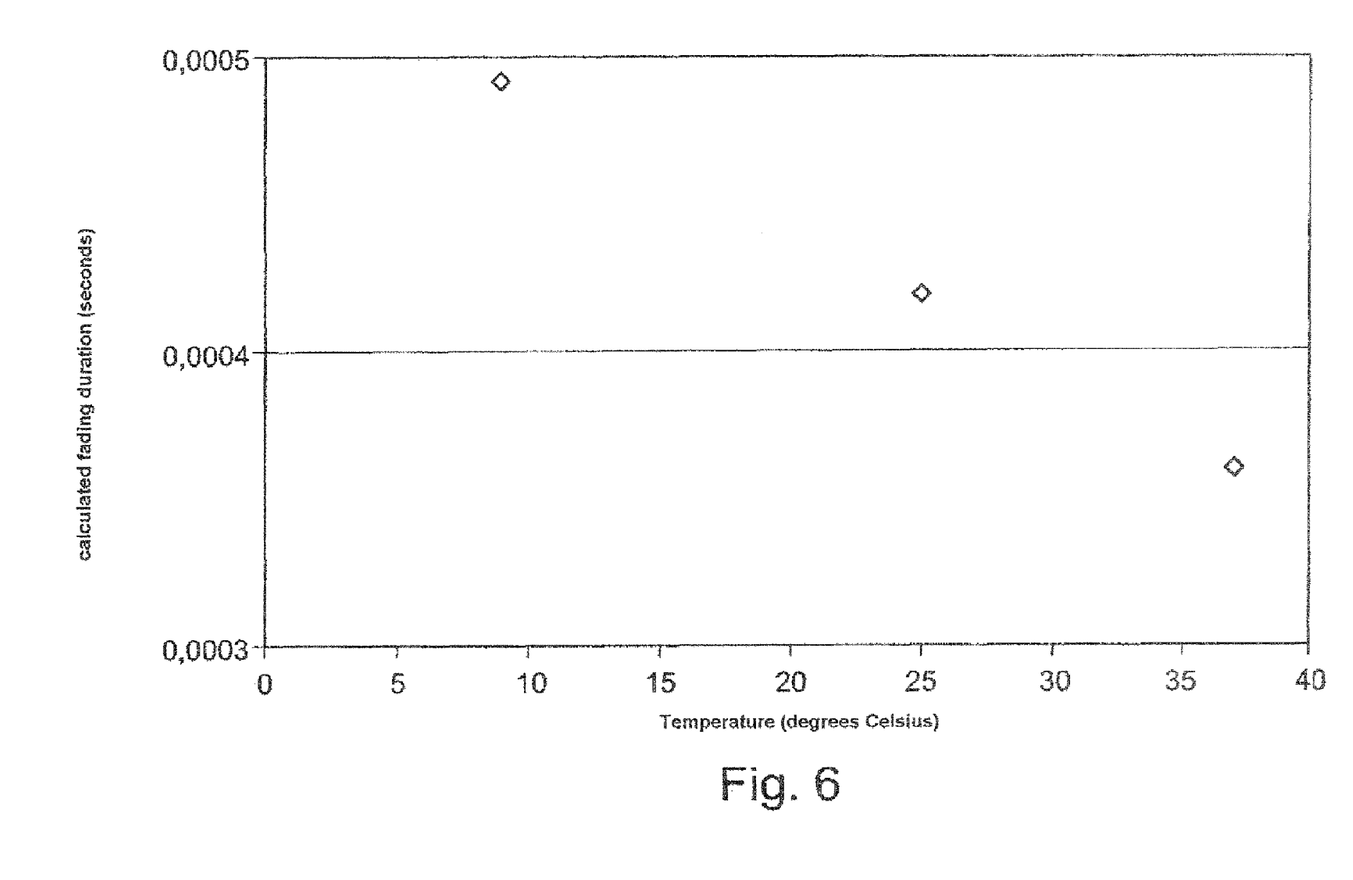
FIG. 6 is a graphic representation for fading times, determined from the measurement results in FIG. 5, as a function of the temperature.

FIG. 6 shows a graphic representation for fading times as a function of temperature, determined from the measurement results in FIG. 5. With an increasing temperature, the fluorescence fading time becomes shorter.

Figure 8:
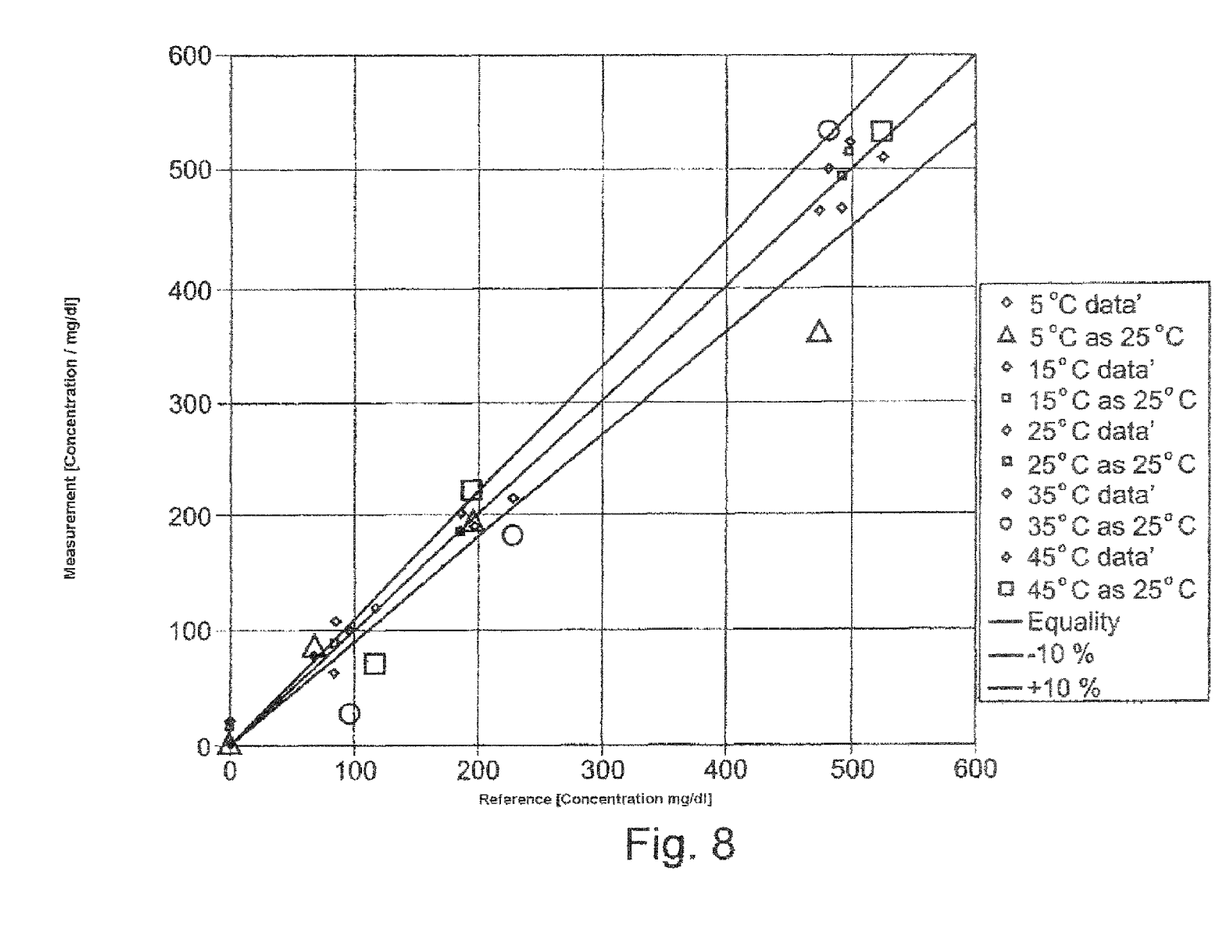
FIG. 8 is a graphic representation of experimentally determined glucose concentrations in blood samples as a function of known reference concentrations.

FIG. 8 shows a graphic representation of experimentally determined glucose concentrations in blood samples as a function of known reference concentrations.

The large symbols (triangles, squares, circles) in FIG. 8 show uncorrected glucose concentration values for the examined blood samples. Compared with this, a measurement correction was carried out for the glucose concentration values represented with small symbols to the effect that the actually present ambient temperature is taken into consideration in the glucose determining. The actual ambient temperature was determined, in accordance with the method previously explained with reference to FIGS. 5 and 6, from the fluorescence behaviour of the added europium complexes. For the glucose concentration values represented by a large triangle in FIG. 8, this means that the originally accepted ambient or measurement temperature was corrected from 25° C. to 5° C. For the glucose concentration values marked by a large circle symbol, the correction took place from 25° C. to 35° C., and for the glucose concentration values shown by the large square symbol, the correction took place from 25° C. to 45° C. It can be seen that the corrected glucose concentration values lie distinctly closer to the central curve course in FIG. 8.

Different methods can be used for the arithmetical correction; for example, experimentally determined sampling points can be determined, between which for example interpolation is carried out linearly, or simply non-linear approximation functions can be determined, which manage with few sampling points.

FIGS. 9a, 9b show structural formulae of further europium complexes which are able to be used as function element.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A test element for evaluating a body fluid or component thereof, the test element including a detection zone which is charged with a reagent sensitive to the body fluid or component thereof by means of a detection reaction configured for determination of a measurement value for the body fluid or component thereof, the test element further including function elements arranged at one or both of the detection zone and adjacent to the detection zone, the function elements being configured for conducting a plurality of status measurements for evaluating and registering at least one status parameter for the detection zone and at least one test element parameter for the condition of the test element, wherein the function elements are sensitive respectively to the status parameter and the test element parameter, wherein the test element is configured to provide a corrected measurement value from the measurement value in consideration of the status measurements.

2. The test element according to claim 1, wherein the function elements are inert with respect to the detection reaction.

3. The test element according to claim 1, wherein the at least one status parameter comprises a reaction parameter of the detection reaction.

4. The test element according to claim 1, wherein the at lease one test element parameter relates to an indication of functional integrity of the test element.

5. The test element according to claim 1, wherein the function elements are configured to be evaluated by means of an optical status measurement.

6. The test element according to claim 5, wherein the optical status measurement comprises a time-resolved optical status measurement.

7. The test element according to claim 5, wherein the optical status measurement comprises an intensity-dependent optical status measurement.

8. The test element according to claim 1, wherein the function elements are mixed at least partly with the reagent.

9. The test element according to claim 1, wherein the function elements are arranged in several zones which are separated spatially from each other.

10. The test element according to claim 1, further comprising a further function element arranged in one or both of the detection zone and adjacent thereto, the further function element being configured for conducting a further status measurement for evaluating and registering at least one further status parameter for the detection zone, wherein the function element is sensitive to the further status parameter, wherein the test element is configured to provide a corrected measurement value from the measurement value in consideration of the at least one status parameter and the at least one further status parameter.

11. The test element according to claim 1, wherein the detection zone determines blood sugar in the body fluid when the body fluid is placed in the detection zone.

12. A measurement method for a test element that is configured for evaluating a body fluid or component thereof, the test element including a detection zone charged with a reagent sensitive to the body fluid or component thereof by means of a detection reaction with the body fluid or component thereof, the method comprising conducting a plurality of status measurements comprising evaluating measurement signals from function elements arranged at one or both of the detection zone and adjacent thereto; registering one or more status parameters for the detection zone and one or more test element parameters for the condition of the test element indicated by the status measurements; determining a measurement value for the body fluid or component thereof from the detection reaction; and providing a corrected measurement value from the measurement value in consideration of the registered status measurements.

13. The method according to claim 12, wherein the one or more status parameters comprise a reaction parameter for the detection reaction.

14. The method according to claim 12, wherein the one or more test element parameters relate to an indication of the functional integrity for the test element.

15. The method according to claim 12, wherein the determining step comprises comparing the measurement value with comparative values.

16. The method according to claim 12, further comprising the step of altering reaction parameters influencing the detection reaction on the basis of the one or more status parameters indicated by the status measurements.

17. The method according to claim 12, wherein the status measurement conducting step comprises carrying out an optical measurement comprising measuring optical measurement signals.

18. The method according to claim 12, wherein the test element is configured for determining blood glucose in the body fluid.

* * * * *